United States Patent
Guglielmi et al.

[11] Patent Number: 6,011,995
[45] Date of Patent: Jan. 4, 2000

[54] ENDOVASCULAR DEVICE FOR HYPERTHERMIA AND ANGIOPLASTY AND METHOD FOR USING THE SAME

[75] Inventors: Guido Guglielmi, Santa Monica; Cheng Ji, Los Angeles, both of Calif.

[73] Assignee: The Regents of the University of California, Oakland, Calif.

[21] Appl. No.: 08/998,589

[22] Filed: Dec. 29, 1997

[51] Int. Cl.[7] .................................................. A61B 17/38
[52] U.S. Cl. .............................. 607/99; 606/29; 607/113
[58] Field of Search ........................... 607/98–99, 113; 606/27, 28–31

[56] References Cited

U.S. PATENT DOCUMENTS

| | | | |
|---|---|---|---|
| 5,118,602 | 6/1992 | Nichols | 604/113 |
| 5,213,097 | 5/1993 | Zeindler . | |
| 5,445,635 | 8/1995 | Denen et al. | 606/27 |
| 5,498,261 | 3/1996 | Strul | 606/29 |

*Primary Examiner*—Lee Cohen
*Assistant Examiner*—Roy Gibson
*Attorney, Agent, or Firm*—Daniel L. Dawes

[57] ABSTRACT

Hyperthermic treatment of tissue such as cancer tumors, is realized by providing an ohmic heating element on the distal tip of a catheter endovascularly inserted upstream of the tissue. Electrical power is provided to the element for a selected time and degree to raise the temperature of blood to a thermally mediating level such as 42° C., but not to heat the blood so that distal tissues downstream are adversely affected. The element comprises a helical coil heater disposed proximate to the end of a catheter and within an expandable cage. The cage can be selectively deployed by expanding it to maintain the coil out of contact with the vessel walls while still allowing free blood flow. Alternatively a guidewire within an expandable cage can be disposed within the same catheter wherein the heating coil has been wound onto the guidewire or the guidewire is uninsulated at that portion within the cage serves as an electrode to directly heat the blood. Angioplasty without blood flow blockage is realized by expanding a cage instead of a balloon on the catheter. The cage can be selectively expanded by withdrawal of a guidewire temporarily coupled to the catheter tip. The cage can widen the narrowed vascular lumen while still allowing free blood flow and/or contrast agent, and it avoids the risk of balloon deflation failure. The expandable cage can be detachable and implantable as a stent.

5 Claims, 11 Drawing Sheets

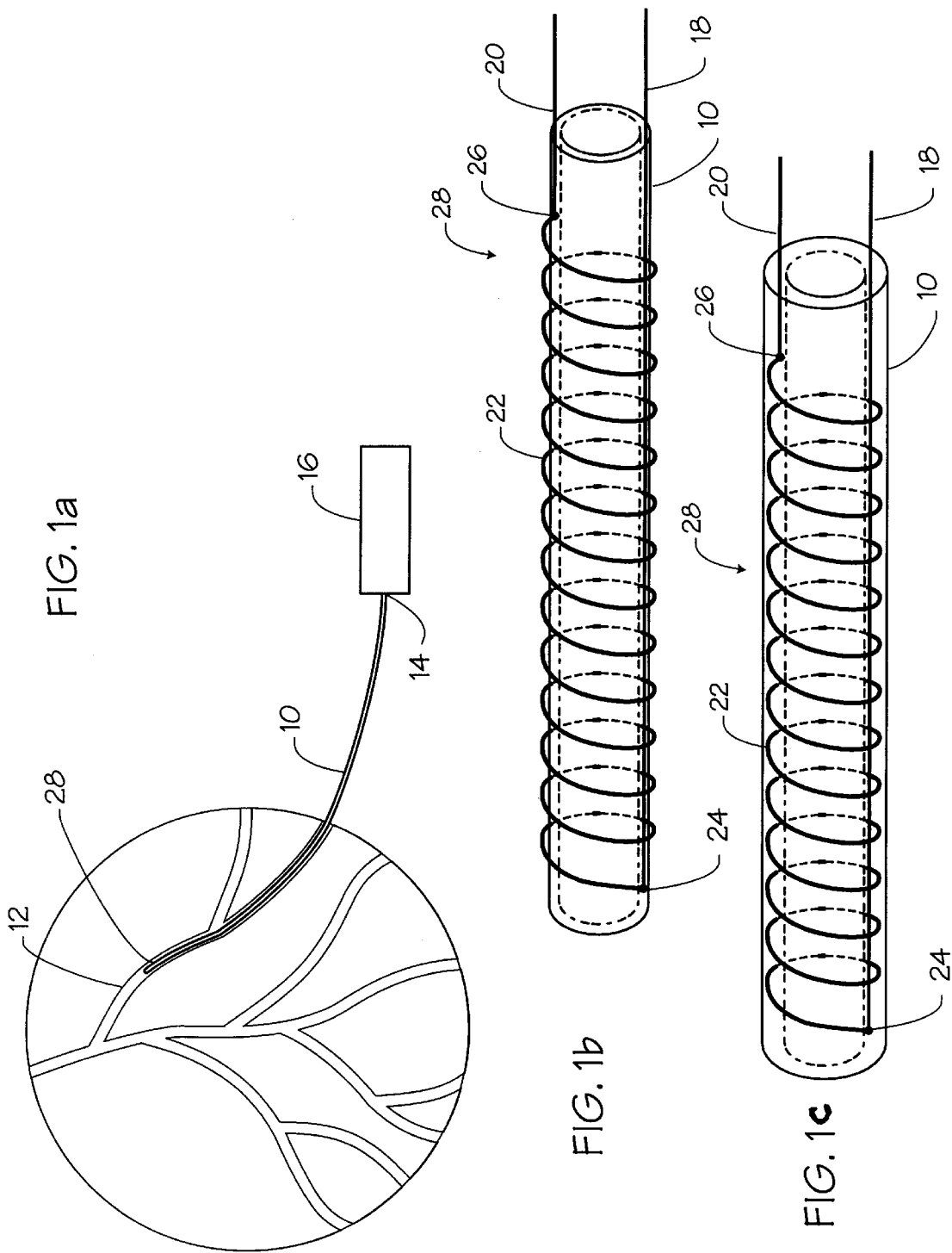

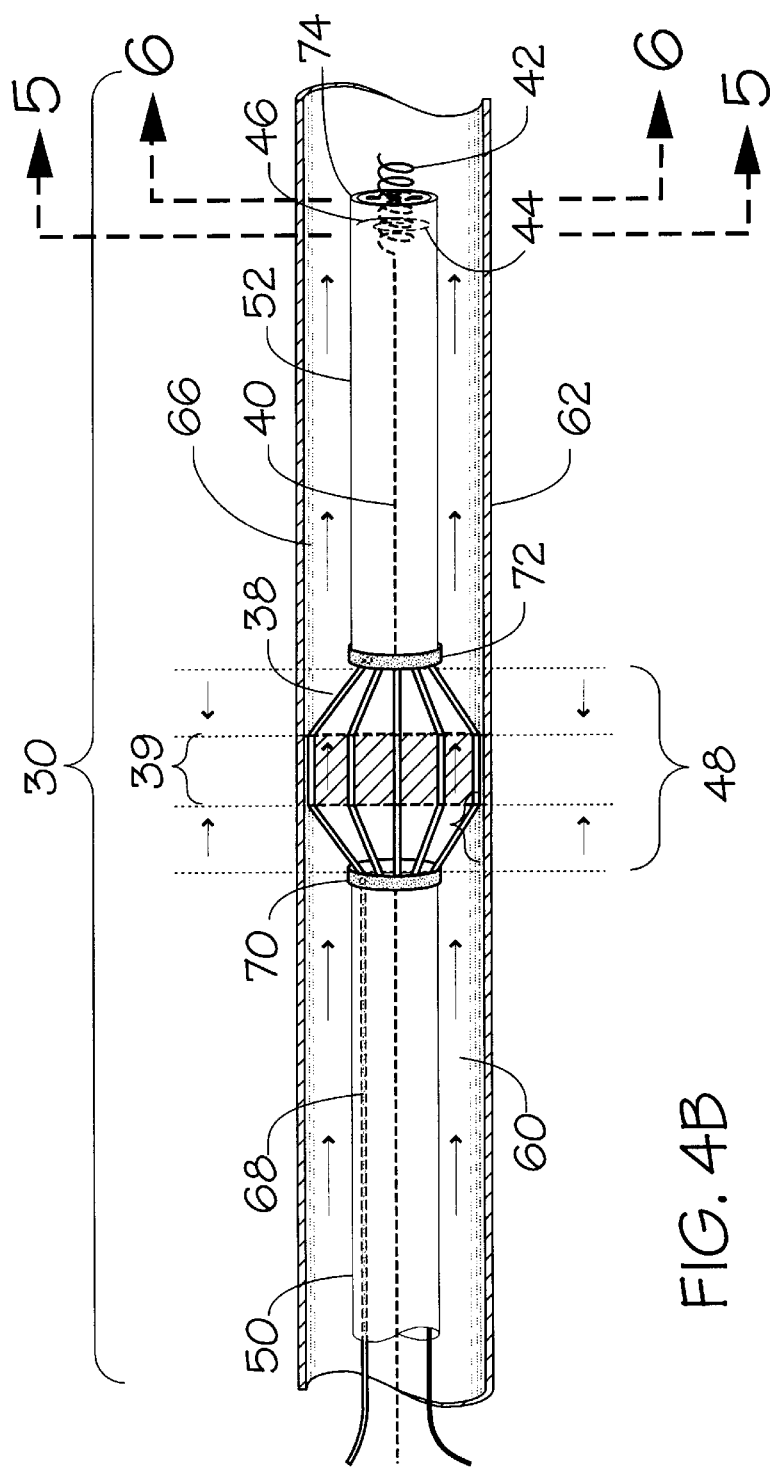
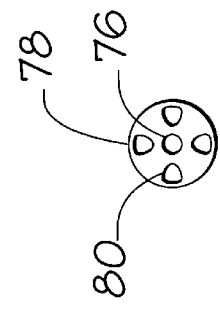
FIG. 4B
FIG. 5
FIG. 6

ENDOVASCULAR DEVICE FOR HYPERTHERMIA AND ANGIOPLASTY AND METHOD FOR USING THE SAME

BACKGROUND OF THE INVENTION

1. Field of the Invention

The invention relates to the field of endovascular devices and in particular to devices used to control blood heating for selective heat treatment of tissue, such as for cancer treatment.

2. Description of Prior Art

The use of hyperthermia for preferential killing of malignant cancer cells is well known. While cancer cells themselves may not be more heat sensitive than normal cells, their environments render them so, namely cancer tissues are normally subject to nutritional deprivation, low pH and chronic hypoxia. It is also apparent that the use of heat has a synergistic effect with x-ray radiation and with cytotoxicity of many anti cancer drugs. Because of the cooling action of blood flow, heating of solid tumors and other vascular lesions can be difficult to arrange and varies with the variable blood flow characteristics.

Blood flow plays an extremely important role in determining the response of tumors to localized hyperthermia. First of all, blood flow can dramatically affect temperature distributions. This is not surprising because the removal of heat from the tumor volume is primarily carried out by blood flow and therefore nonuniform blood flow invariably results in nonuniform temperature distributions. Furthermore, blood flow does not remain constant during heat treatment. In normal tissue, the body increases flow within the heated volume in an attempt to affect cooling. Some tumors, although not all, behave similarly. In other tumors, this homeostatic control response is either reduced or missing altogether. After extended periods of heating of greater than 30 minutes and particularly at temperatures of 43° C. or higher, blood flow in some murine tumors stops almost entirely. For these reasons, temperature monitoring during heating is essential. Finally, blood flow to a large extent determines the availability of tumor cells of oxygen, nutrients as well as drugs during chemotherapy. All these can influence the response of cells within tumors to treatments.

The killing of cells is highly effective with respect to temperature. The change of even one degree C can cause appreciable differences in cell killing rates. However, when heat alone is relied upon for treatment, either the treatment temperature must be so high that sufficient cell killing occurs even in the cold spots within the cancerous tissue or the temperature uniformity within the heating tumor must be maintained at a predetermined magnitude to within about a degree C. Each of these approaches entailed great technical difficulties.

In those tumors where blood flow is highly nonuniform, avoidance of cold spots becomes a particularly difficult problem. If any major blood flow vessels traverse the lesion, then uniform heating is probably impossible. Blood flow in those vessels is so great that in their vicinity some degree of cooling is inevitable. In addition to blood flow, the mode of heating can create nonuniform temperature distributions.

Some cancers are so virulent that survival of one or at most a few of these cells can lead to regrowth of the tumor and hence failure of the treatment. Obviously, then, if the heated tumor contains even small volumes of inadequately heated sections, its eradication by hyperthermia becomes highly unlikely, particularly when it is kept in mind that one gram of tissue contains approximately tens of millions of cells.

Methods of inducing hyperthermia can be divided into two broad categories. In regional heating, energy is deposited in general volume containing the tumor. Some special characteristics of the tumor, such as reduced blood flow compared that in the surrounding normal tissues, is relied upon for the tumor to reach the therapeutic temperature while the normal tissues remain cool.

In focused heating, the energy is deposited directly within the tumor. Less reliance is placed on the differences between the tumor and normal tissues, but the special definition of the energy deposition must be much more precise. A number of methods of focused heating have been suggested including noninvasive technique of focused ultrasound and invasive techniques of interstitial radio frequency currents, interstitial microwave antennas, and use of lossy magnetic material to preferentially absorb energy from an external electromagnetic field.

The implantation of lossy magnetic materials, which are then localized and heated in place, is limited by the magnetic characteristics of the materials, the ability to secure them into a localized position and the long term effects of their presence, since in most cases they cannot be removed or are only very slowly dispersed from the implantation site.

Interstitial implantation of heated fluid has also been utilized through delivery catheters. However, the amount of heated fluid that can be delivered to the tumor site as well as the length of time in which the tumor can be heated is limited since the capacity for fluid absorption in any tissue, particularly denser tissue such as brain tissue, is necessarily limited.

If ultrasound is used to deposit energy within the tumor volume, shielding by bony structure may prevent heating in some volumes. Bones also reflect ultrasound, thereby also contributing to nonuniformities. Bones are reasonably good conductors of heat and therefore near bones, areas of low temperature may be encountered.

Nonuniformity of either electric field strength of current density can also result in the occurrence of cold spots when dielectric heating techniques are used. These result from nonuniform power deposition patterns, or from nonuniform absorption characteristics of the tissue irradiated.

Therefore, what is needed is some means which is not subject to the defects of the prior art but which will allow localized heating in both degree and time for the effective therapeutic treatment of tissue.

BRIEF SUMMARY OF THE INVENTION

The invention is an apparatus for hyperthermic treatment of tissue comprising an elongate member having a distal and proximal end, the distal end adapted to be positioned in the artery proximate to the tissue and thermally coupled thereto. An ohmic heating element is disposed on the elongated member at or proximate to the distal end. The ohmic heating element is in direct contact with fluid or blood normally flowing to the tissue so that the tissue is subjected to a controlled amount of heat at a selected temperature for a selected amount of time.

The apparatus further comprises an expandable structure for selectively maintaining the heating element in a spaced apart relationship from the vascular walls.

In one embodiment the elongated member comprises a catheter and the ohmic heating element is a coil heating element wound about the catheter. The coil heating element has two ends, which are coupled to supply wires disposed in lumens in the catheter. The heating coil may be insulated if the coil is disposed on the exterior surface of the catheter or uninsulated if the coil is disposed within the catheter, the catheter wall or between cylindrical layers which comprise the catheter. The apparatus may further comprise a temperature sensor to detect temperature of the fluid downstream from the ohmic heating element.

In one embodiment the elongated member is a single catheter and the ohmic heating element comprises a coil spring heating element and a surrounding expandable cage disposed about the coil spring heating element to retain the heating element out of direct contact with surrounding solid tissue. The coil spring heating element is uninsulated and the surrounding cage is partially insulated. The coil is electrically coupled in circuit with the cage. The catheter includes a first current supply line electrically coupled to the coil and a second current supply line electrically coupled to the cage. The current supply lines extend to the proximal end of the catheter.

The apparatus further comprises a guidewire disposed through the catheter. The catheter is comprised of a first proximal and second distal portion which are relatively telescopic with respect to each other, i.e. they may be moved toward or away from each other. The first and second portion are longitudinally displaced toward or away from each other by means of the guidewire. The guidewire is slidable within the first portion, coupled to the second portion, and adapted to draw the first and second portions of the catheters together when tensile force is applied to the guidewire from the proximal end of the catheter or push the first and second portions of the catheters apart, thereby expanding or contracting the cage respectively. The guide wire may further comprise a temperature sensor to detect the blood flow temperature downstream.

The cage comprises a plurality of elements having at least one portion lying in common on a cylindrical envelope in which the heating coil is interiorally disposed. The portions of the cage lying on the cylindrical envelope are parallel to the axis of the catheter.

In another embodiment the cage is a prebiased spiral adapted to assume a radially expanded envelope when the first and second portions of the catheter are drawn together.

The guidewire is selectively engagable with the second portion, e.g. the distal portion, of the catheter, and in particular is threadably coupled to second portion of the catheter.

In another embodiment the ohmic heating element comprises at least a portion of a guidewire. Still further a portion of the guidewire acting as the ohmic heating element comprises an ohmic heating coil wound on the guidewire as a form. The ohmic heating element is a guidewire having at least a portion thereof noninsulated and an expandable cage on the catheter in which the noninsulated portion of the guidewire is disposed. The elongated member is a catheter and the guidewire be disposed in the catheter. The guidewire has three versions: (1) namely a monopolar embodiment in which the heating coil is wound on the guide wire as a single helix and in which the electrical circuit is completed through the tissue to a body electrode; (2) a first bipolar embodiment in which the heating coil is spirally wound on the guide wire in the form of two separated wires forming a double helix, which wires are insulated and connected to each other at their distal ends to form a closed circuit; and (3) a second bipolar embodiment in which the heating coil is spirally wound on the guide wire in the form of two separated wires forming a double helix, which wires are uninsulated and not connected to each other, and in which the electrical circuit is completed by current flowing through the blood or fluid between adjacent wraps of the two separated wires.

The invention is also defined as a method for hyperthermically treating tissue comprising the steps of providing an elongated member with a ohmic heating element included within a distal portion of the elongated member. The distal portion of the elongated member is disposed proximate to tissue to be treated at a position thermally coupled to the tissue through blood or fluid flow thereto. The distal portion of the elongated member is maintained out of contact with surrounding tissue, which is usually the vessel wall, except for the fluid flowing by the distal portion of the elongated member. Power is selectively provided to the ohmic element to heat fluid flowing by the heating element to the tissue to be treated. The step of maintaining the distal portion of the elongated member out of contact with surrounding tissue except for the fluid flowing by the distal portion of the elongated member comprises the step of deploying an expandable cage around the ohmic heating element. The step of deploying an expandable cage around the ohmic heating element comprises the step of longitudinally drawing a distal portion of the elongate member toward the proximal end of the elongate member to shorten the expandable cage thereby radially extending the expandable cage deployed about the ohmic heating element without substantially radially extending the ohmic heating element.

Still further, the invention is defined as an apparatus for vascular angioplasty comprising an elongate member having a distal and proximal end. the distal end having a tip is displaceable toward and away from the proximate end. A radially expandable cage is coupled between the tip and the proximal end of the elongate member. A guidewire is coupled between the tip and the proximal end of the elongate member. The guidewire selectively displaces the tip toward or away from proximal end and for selectively radially expanding and contacting the cage.

In one embodiment the cage expands radially to form a cylindrical barrel shape when the guidewire is withdrawn to displace the tip toward the proximal end. In another embodiment the cage expands radially to form a biconical shape when the guidewire is withdrawn to displace the tip toward the proximal end.

In another embodiment the cage may combine the above two shapes, which means that the cage can be formed in two layers. The inner layer forms a cylindrical barrel shape, and the outer layer forms a biconical shape. Both the inner and outer layers of the cage expand together when the guidewire is withdrawn or tensioned. This combination increases the expansive force and may be optimal for use in angioplasty of the sclered or calcified vessel wall. It is further contemplated that the outer layer may be selectively detachable so it is left in place as a permanent stent.

The invention and its various embodiments may now be better visualized by turning to the following drawing wherein like elements are referenced by like numerals.

BRIEF DESCRIPTION OF THE DRAWING

FIG. 1A is a simplified block diagram showing the environment of the invention and its use to treat a vascular tumor.

FIG. 1B is a elevational diagrammatic side cut-away view in enlarged scale of the distal portion of a first embodiment of the invention shown in enlarged scale in which the heating coil is mounted on a catheter tip.

FIG. 1C is a elevational diagrammatic side cut-away view in enlarged scale of the distal portion of a second embodiment of the invention shown in enlarged scale in which the heating coil is mounted inside of a catheter tip.

FIG. 4B is a side elevational view subsequent to deployment of the embodiment of FIG. 4A.

FIG. 5 is an end elevational view of the catheter of FIG. 4A as seen through section lines 5—5 of FIG. 4A or 4B.

FIG. 6 is an end elevational view of the catheter of FIGS. 4A and 4B as seen through section line 6—6 of FIGS. 4A and 4B.

Figure 2A:
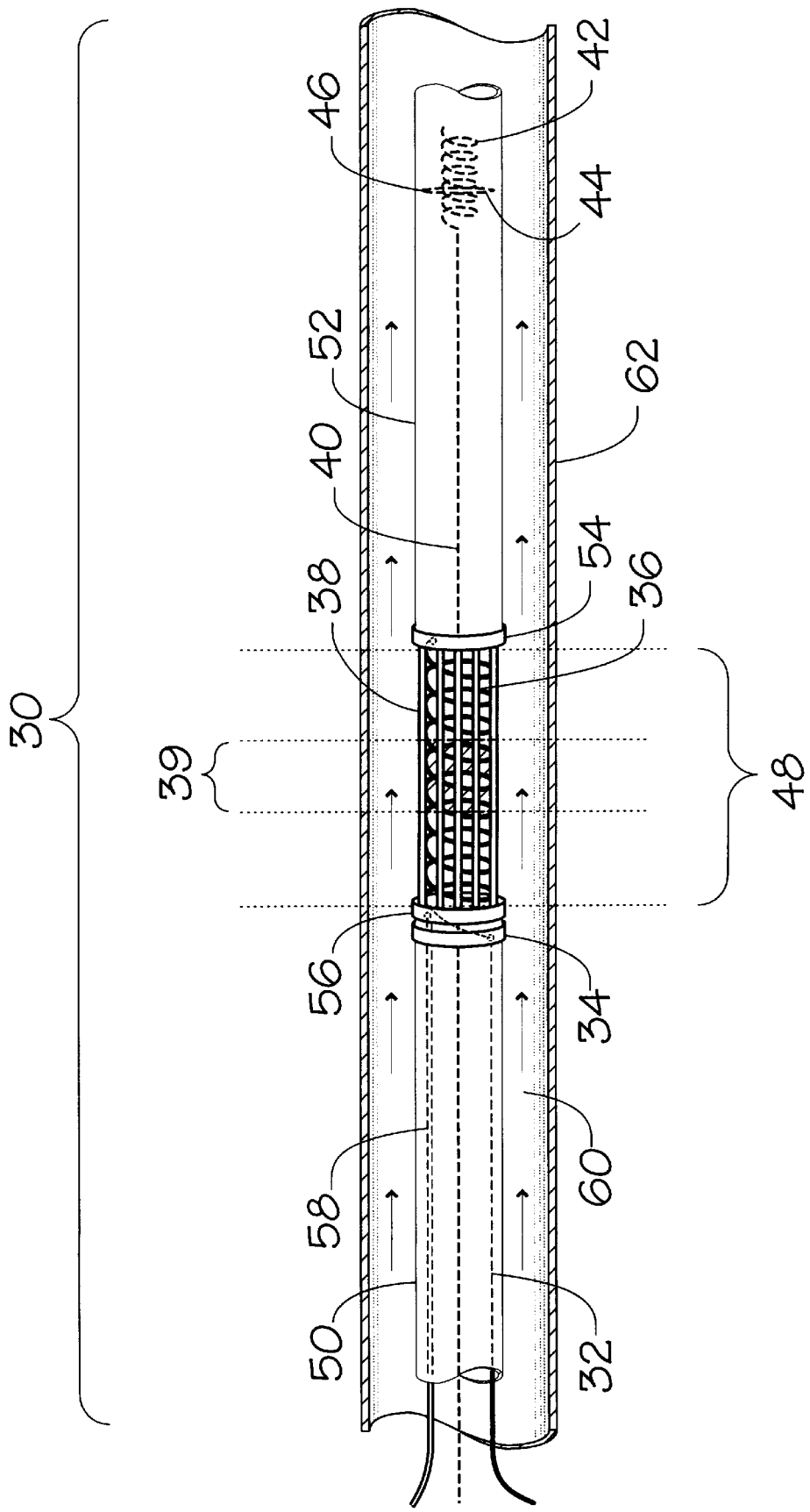
FIG. 2A is a simplified sectional side view of another embodiment of the invention shown in a configuration prior to deployment.

The invention and its various embodiments may now be better understood by turning to the following detailed description.

DETAILED DESCRIPTION OF THE PREFERRED EMBODIMENTS

Hyperthermic treatment of tissue and in particular cancer tumors, is realized by providing an ohmic heating element on the distal tip of a catheter, which is endovascularly inserted just upstream of the cancer tissue. AC or DC power is provided to the ohmic element for a selected time and to a selected degree to raise the temperature of blood flowing into the cancer tissue to a thermally mediating level such as 42° C., but not heating the blood to such an extent that more distal tissues downstream are adversely affected. The heating element may include a helical coil heater on a catheter, or heater coils that are disposed proximate to the end of the catheter and within an expandable cage. The cage can be selectively deployed by opening and expanding it to maintain the heating coil out of contact with the vessel walls while still allowing free access to blood flow. In addition to have a heating coil within an expandable cage in a catheter, it is also possible to use a guidewire disposed within the same catheter and also within an expandable cage wherein the heating coil has been wound onto the guidewire as a form the guidewire is uninsulated at the portion within the cage as an electrode to provide ohmic heating directly in the surrounding blood.

FIG. 1A is a diagrammatic side view in expanded scale of a first embodiment of the invention showing a heating catheter or instrument, generally denoted by reference numeral 10, having a distal portion 28 disposed in body 12 and a proximate portion of which extends from the application site, typically an endovascular site, to a position outside body 14 wherein instrument 10 is coupled to a source of electrical current and other sensing or measurement circuits 16 as may be utilized by one having ordinary skill in the art for determining and controlling the flow of current, voltages, power and temperatures achieved in instrument 10. For example, although not depicted instrument 10 may also be provided with temperature sensors at one or more points along its distal portion for monitoring the delivery of heat into the fluid or blood. FIG. 1B shows in highly diagrammatic form the distal portion 18 of instrument 10 in enlarged scale. Although greater detail of circuits 16 will be discussed below, the nature and performance of circuits which may be used in combination with instrument 10 is largely secondary to the invention and therefore will not be described in greater detail.

FIGS. 1B and 1C are simplified side perspective views of the tip portion 28 of catheter 10 shown in a cut-away view in enlarged scale. As shown in FIG. 1B instrument or catheter 10 is comprised of a first elongate member 18 comprised, for example, of a low resistance flexible metal wire. A second elongate member 20, which is essentially identical to first member 18, is disposed generally parallel to member 18 and thus provide two sides of a circuit to instrumentation 16. Wires 18 and 20 are preferably insulated floppy wires with a low electrical resistance as compared to electrical heating coil 22, but may comprise uninsulated wires disposed in lumens or embedded in the wall of catheter 10. Electrical heating coil 22 is coupled between elongate members 18 and 20 and is diagrammatically shown in FIG. 1B as spirally wound about catheter 10. Heating coil 22 is connected at its end 24 to elongate member 18 and at its distal end 26 to elongate member 20.

AC or DC current is supplied through elongate member 18 to connection 24, to coil 22 and hence to connection 26 and returned to circuits 16 along elongate member 20. Heating coil 22 is made of a high resistance material, such as platinum, so that substantially all of the ohmic heating which occurs in instrument 10 occurs in heating coil 22 with little if any heating occurring in either elongate members 18 or 20.

In the illustrated embodiment if the elongate members 18 and 20 may be insulated electrically from each other and hence from coil 22 to prevent heating through any circuit path other than through connection points 24 and 26 to heating coil 22. In an alternative embodiment elongate members 18 and 20 may be uninsulated while heating coil 22 remains insulated and while elongate members 18 and 22 are maintained apart from coil 22 by being mounted on an insulating flexible longitudinal strip or within catheter 10. In the embodiment of FIG. 1B coil 22 is exterior to catheter 10 and hence in direct thermal contact with the blood or fluid, while in the embodiment of FIG. 1C coil 22 is interior to catheter 10 and hence in indirect thermal contact with the blood or fluid.

For example, in one embodiment of the invention of FIG. 1, elongate members 18 and 20 are flexible copper insulated wires having a diameter of 0.020–0.002 inch, and catheter 10 has a diameter of 3–7 French, while heating coil 22 is insulated platinum wire of 0.020–0.002 inch diameter tightly wound about the distal tip 28 of catheter 10. Where mounted on the exterior of catheter 10 the assembly of wires 18 and 20 and/or heating coil 22 in turn may be encapsulated or disposed within a thin insulating coating or adhesive for physical integrity although the thickness of the coating will be limited to ensure that thermal conduction is not materially impeded in any way. A DC or AC signal of 2–300 watts is applied at to heating coil 22, which can quickly raise the temperature of distal portion 28 of instrument 10 to heat the temperature of flowing fluid or blood in contact with distal portion 28 to 42° C. and higher within ten to fifteen seconds.

Although the currents, voltages, wire sizes and choices of material have been discussed above illustratively, it must be understood that many other substitutions can be made without making any substantial difference in the invention. Flexible metallic alloys can be employed for both wire members 18 and 20 as well as heating coil 22 and their resistances modified by choice of materials or impurities provided in a base conductor so that instrument 10 has a size and flexibility adapted for insertion in the smallest endovascular other bodily cavities or systems. The device can be incorporated in a sterile catheter or otherwise modified according to conventional techniques so that it can be selectively placed at any site within the body and in particular in the endovascular system including any neurological sites. Because a catheter system would be then deployed in body lumens or blood vessels of limited blood flow and having diameters not that much greater than instrument 10 itself, the temperature rise within the body of lumen can be increased rapidly and variably controlled to a predetermined temperature for arbitrary selected times according to therapeutic choice. Thus even dense cancerous tissue masses which were heretofore difficult to thermally mediate, become thermally mediatable in a highly controlled manner by endovascular placement of instrument 10 at the vascular input or portal to the cancerous tumor. The amount of heat input through instrument 10 to the tumor can then be monitored and carefully controlled to the degree required and for the time desired notwithstanding highly variable conditions between one tumor site and another within a tumor from one time to another. The thermal effect is completely expended within the immediately adjacent tumor site fed by the vascular system without the introduction of any extraneous fluid or substance, without reflections or focusing difficulties, without burn potential and without any uncontrollable adverse effect to more distant downstream healthy tissue.

The temperature developed within distal end 28 or at any other point within the target tissue may be determined by any means now known or later described including infrared tomography. In addition to noninvasive scanning techniques, instrument 10 as stated above may include one or more temperature sensors within distal portion 28 or adjacent thereto. For example, a separate temperature sensor could be provided and connected through it is own wires to either one or both of elongate members 18 and 20 or disposed within one of them. Members 18 and 20 may also be used for carrying a separate monitoring signal at a distinct frequency. It is still further possible that the resistivity of heating coil 22 may be a function of temperature and can be deduced by monitoring current at a fixed or calibrated voltage through instrumentation 16. For example, the resistivity of either heating coil 22 or the wires within elongate members 18 and 20 at a particular frequency may be temperature sensitive so that electrical power for heating is provided at a different frequency and can be easily distinguished from the monitoring frequency. The detector could include a small semiconductor detector mounted on the exterior of either elongate members 18 and 20 in direct contact with the exterior fluid so that it would be measure the heat delivered to the exterior fluid as opposed to the temperature of heating coil 22. The invention should not be understood as limited by the particular means or methodology by which the temperature is monitored. Power supplied to coil 22 is thus controlled by conventional means in circuit 16 through a feedback signal either direct or indirectly generated by the temperature of the downstream blood flow or tissues.

FIG. 2A is a side cross sectional view in diagrammatic form of a second embodiment of the invention showing a catheter instrument generally denoted by reference numeral 30 carrying an uninsulated wire 32 inside of the nonconducting body of catheter 30 to a conduction band or terminal point 34. An insulated or partially insulated helical heating coil 36 is then disposed within a cylindrical barrel or bird cage 38 of insulated or partially insulated wires. The wires of cage 38 may be uninsulated except for the segments at or near the central section 39 where cage 38 may contact the vessel walls. In the case where cage 38 carries some or all of the heating current, this insulation may be required to avoid creating hot spots or burning the vessel walls. In the embodiments of the invention where cage 38 carries no current, cage 38 may be entirely uninsulated or made of nonconductive material such as plastics. The wires of cage 38 are connected at their opposing ends between a proximal portion 50 and a distal portion 52 of catheter 30. A guidewire 40 is disposed through catheter 30 and includes an end attachment or threaded end 42 engaged with a threaded or bored plate or threaded device 44, such as a mating helical coil fixed within catheter 30 at position 46. The means by which guidewire 40 is selectively coupled and uncoupled to device 44 is secondary to the invention and will be briefly described in passing, but must be understood to expressly contemplate any substitution means of temporarily coupling now known or later devised.

By virtue of the inherent structural integrity of each of the elements of catheter 30 including wire cage 38, exposed portion 48 remains in an elongated configuration equal to or less than the outer diameter of catheter 30. Nevertheless, helical coil 36 and cage 38 are exposed to the exterior fluid or blood and extend between a proximal portion 50 and distal portion 52 of catheter 30. The distal end of heating coil 36 is connected to a terminal band or point 54 in portion 52 of catheter 30 to which all of at least one of cage wires 38 are connected. The opposing or proximal end of the wires of cage 38 are similarly connected to a conductive band or terminal point 56 on portion 50 of catheter 30. Terminal 56 is then connected to a return wire 58 leading to exterior circuits 16 as shown in the embodiment of FIG. 1A.

Figure 2B:
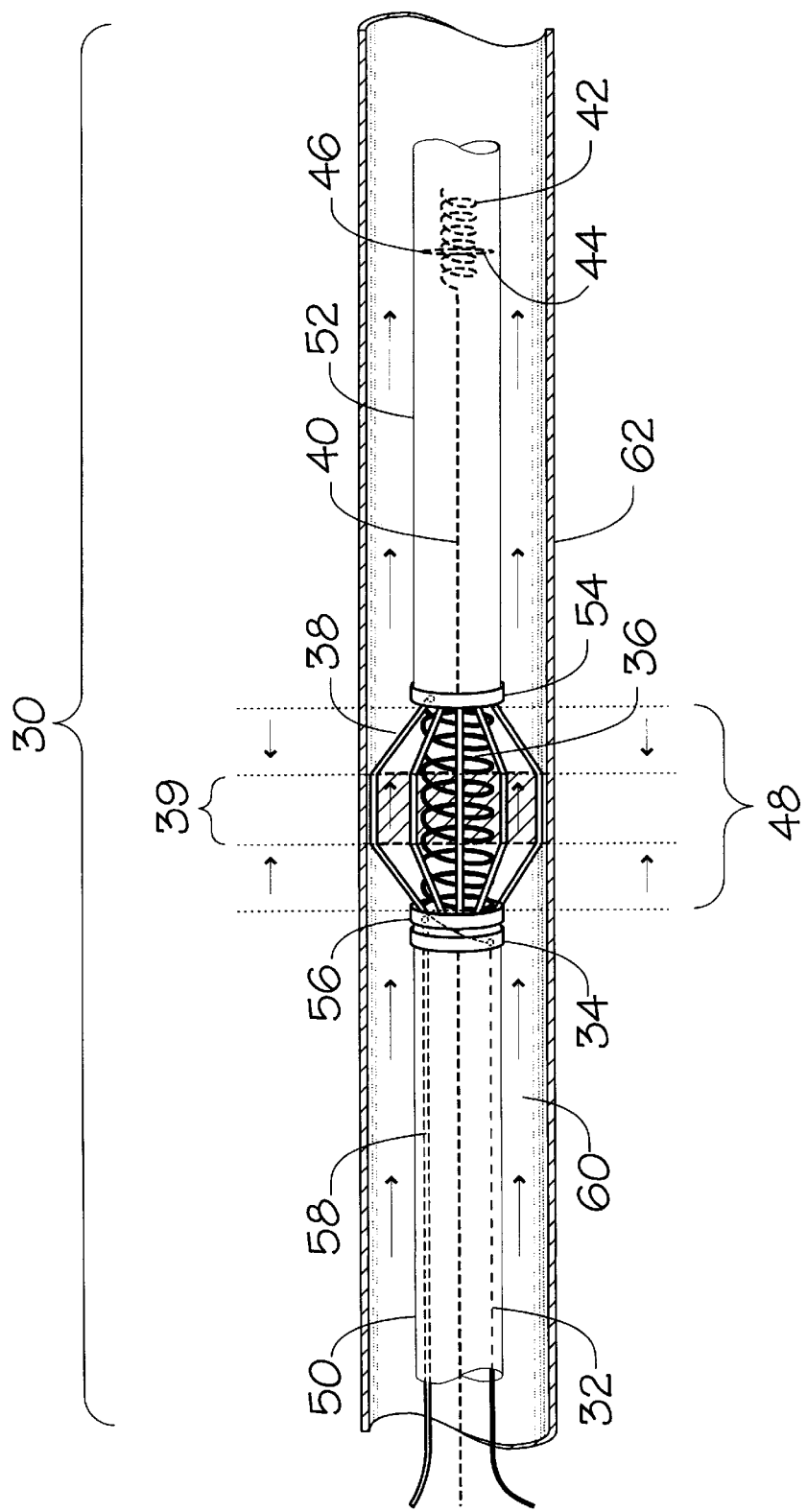
FIG. 2B is a sectional side view of the embodiment of FIG. 2A shown in a configuration after deployment.

When guidewire 40 is coupled to device 44 and pulled by means of a tensile force applied exteriorly to catheter 30, as shown in FIG. 2B, distal portion 52 and proximal portion 50 are drawn together. This causes prebiased cage 38 to expand outwardly to form a cylindrical protective space or cage about heating coil 36. Heating coil 36, which can be visualized as a compression spring with its longitudinal axis parallel to the longitudinal axis of catheter 30, is also compressed thereby decreasing its pitch while its exterior envelope or diameter remains substantially constant. Fluid or blood 60 flowing through vessel 62 freely enters within the space defined within expanded cage 38 and through helical coils 36. However, the exterior of the blood vessel wall is maintained in a spaced relationship away from heating coil 36 thereby preventing burns or shorts which might be otherwise occur if coil 36 were permitted to come into direct contact with the tissue or in the vascular walls.

Based on the main structure of this second embodiment of the invention described above, there are three versions according to their different way of completing the electrical circuit.

In the first version as shown in FIG. 2B, the electrical circuit is completed from circuits 16 through wire 32 to insulated terminal 34 through fully insulated "heating coil" 36, which may be made of a material having a high electrical resistance, such as tungsten, to insulated terminal 54 and back through the fully insulated wires of cage 38, which wires have a low resistance, to insulated terminal 56 and wire 58 to circuits 16. In this way, most of heat will be generated by "heating coil" 36, because coil 36 will have the highest resistance. When the heat conducts from hot coil 36 to the passing by blood or fluid flow 60, its temperature will be raised.

Alternatively, in the second version, as shown in FIG. 2B, the electrical circuit is completed from circuits 16 through wire 32 to insulated terminal 34 to "heating coil" 36, which is insulated except for the segment at or near the central section 39, low resistance, and from the uninsulated central segment of "heating coil" 36 to the passing by blood flow 60 (blood has a much higher resistance than any metallic elements in this device), and through the blood flow 60 back to the uninsulated portion of the wire(s) of cage 38, which wires have a low resistance, and are uninsulated except for the segment at or near the central section 39 where cage 38 may contact the vessel walls, to insulated terminal 56 and wire 58 to circuits 16. In this case, the electric resistive heating will directly generate at the passing by blood flow 60, while neither the "heating coil" 36 nor the cage 38 will be heated directly. Also, different from the first version of this second embodiment of the invention, terminal 54 will be made of nonconductive material, and will have no electricity passing through it.

In the third version as shown in FIG. 2B, the wire(s) of cage 38 can be fully insulated, or can be made of nonconductive material such as plastics. "Heating coil" 36 remains uninsulated and acts as a monopolar probe. The electrical circuit is completed from circuits 16 through wire 32 to terminal 34 to "heating coil" 36, which is uninsulated, or insulated except for the segment at or near the central section 39, which has a low resistance, and exits from "heating coil" 36 to the passing by blood flow 60 and through the biological body back to a conductive ground pad, (not shown) stuck on the shin of the body, and through a return wire from the ground pad back to the circuits 16. In this version, wire 58 is not necessary and can be omitted, and terminal 56, 54, and cage 38 can be made of nonconductive material such as certain polymers. This is because no electricity need to pass through them. The heat will generated directly in the passing by blood flow 60.

After the desired hyperthermic treatment, guidewire 40 is once again advanced, stretching cage wires 38 and coil 36 to reassume an elongated and restricted cylindrical configuration as shown in FIG. 2A. The embodiment in FIGS. 2A and 2B has the additional advantage in that portion 52 of catheter 30 provides a structure within monitoring or temperature sensing devices may be disposed downstream from the heating site. The temperature sensing devices such as a thermal couple can be also integrated on the tip of guidewire 40. The sensing location may be disposed immediately downstream from heating coil 36 so that actual blood temperature that is reached in the near vicinity of coil 36 can be monitored as well as temperatures further downstream which would be indicative of the degree of blood circulation or cooling and hence provide a feedback means for effective therapeutic dosage at the actual tumor site downstream from catheter 30 as well as the magnitude of blood flow. In this way any homeostatic response of the tissue or tumor can be monitored and accommodated.

Figure 3A:
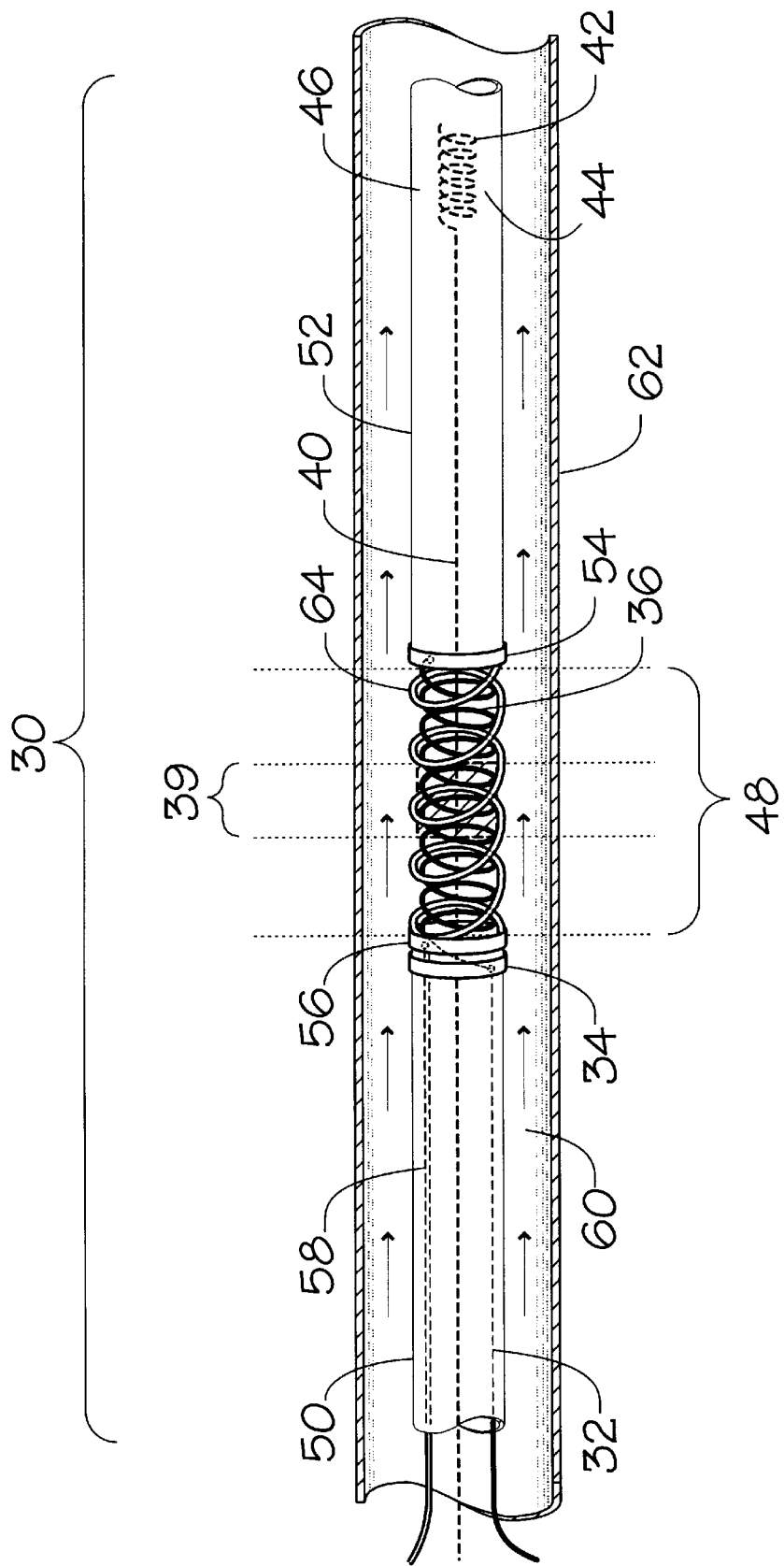
FIG. 3A is a diagrammatic sectional side view of still another embodiment of the invention prior to deployment.
Figure 3B:
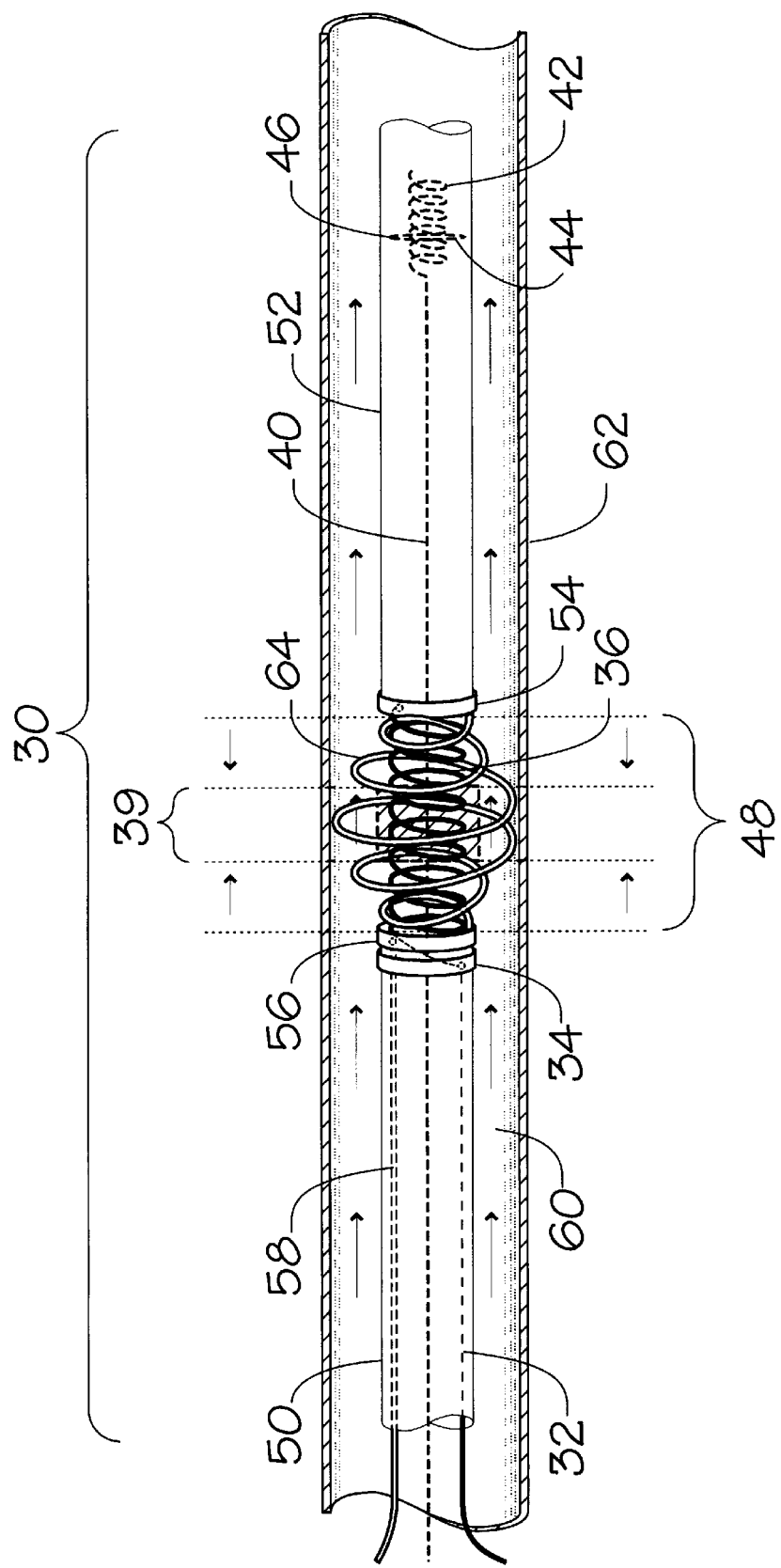
FIG. 3B is a sectional side view of the embodiment of FIG. 3A after deployment.
Figure 3C:
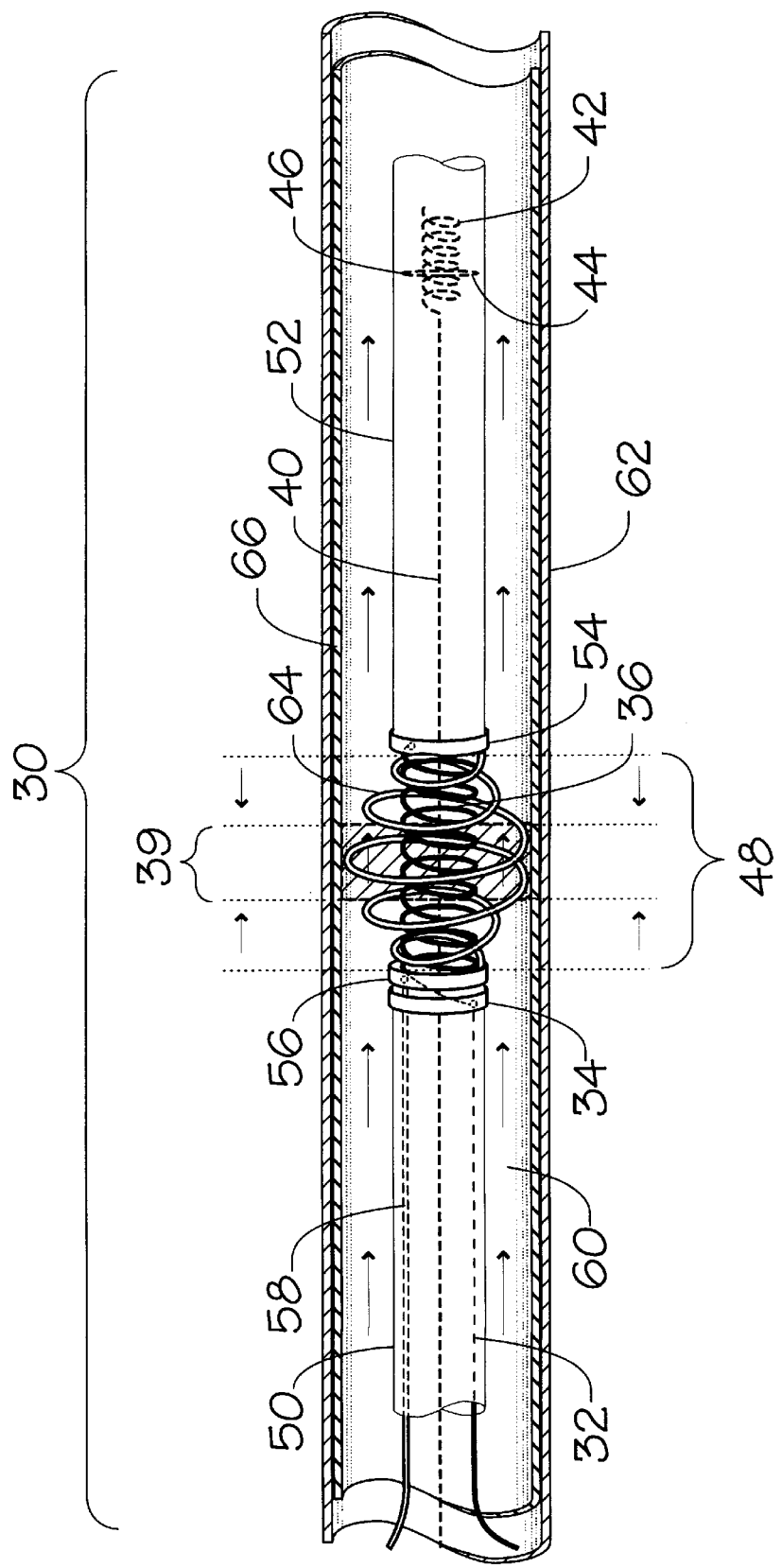
FIG. 3C is a side sectional view of an alternative embodiment of the invention of the FIGS. 3A and 3B after deployment when a portion of the coil has been modified to localized heating.

A third embodiment to the invention is shown in FIG. 3A in which catheter 30 is provided with a different form of the insulating coil and protective cage than that shown in FIGS. 2A and 2B. For example, instead of having a prebiased expandable cylindrical cage 38 of insulated wires, cage 38 is replaced by a prebiased helical form 64. Heating coil 36 remains in the form of a helical coil of substantially fixed diameter. When portions 50 and 52 of catheter 30 are moved towards each other as shown in FIG. 3B, prebiased insulated protecting coil 64 expands to an increased diameter while the pitch of heating coil 36 decreases without substantial radial expansion. Therefore, as shown in FIG. 3C within a vessel 66 insulating expanded cage 64 serves to maintain heating coil 36 spaced apart from the vessel walls. Thus, the cage of wire 64 instead of forming a barrel envelope around heating coil 36 forms a biconical envelope, namely an envelope having a frustoconical cone extending from portion 50 of catheter 30 to a maximum diameter approximately midway between the separate portions 50 and 52 with a frustoconical envelope then decreasing in diameter downward to connection with portion 52 of catheter 30. While heating coil 36 is contemplated as being uninsulated, it is also within the scope of the invention that only the central portion of coil 36 well spaced from vessel walls 62 is uninsulated with the remainder carrying a thin layer of insulating film.

In addition to having utility as a blood heating device, the invention of both FIGS. 2A and 2B and 3A–3C can also be used as appropriate as an angioplastic device where internal mechanical expansion of a vessel 66 is required. The expandable design disclosed in the present invention has the advantage of minimal interference with blood flow and simplicity of the means for providing expansion and contraction as opposed to the more complicated and sometimes more unreliable difficulties in inflation and deflation of an angioplastic balloon. For example, when an angioplastic balloon expands it entirely blocks the blood flow whereas in the present invention the expanded cage 38 or 64 allows the blood to continue to flow through vessel 66 substantially unimpeded by virtue of the expansion. Where the angioplastic device must be some reason must remain in the vessel for an extended time period, this flow blockage can become unacceptable. In addition, any case where the angioplastic balloon should be difficult or impossible to deflate because of a malfunction, serious medical consequences can result arising from the long term blockage of flow to downstream tissues. Such a consequence does not occur in connection with the use of the present invention should contraction of the cage be difficult or delayed because of malfunction.

Figure 4A:
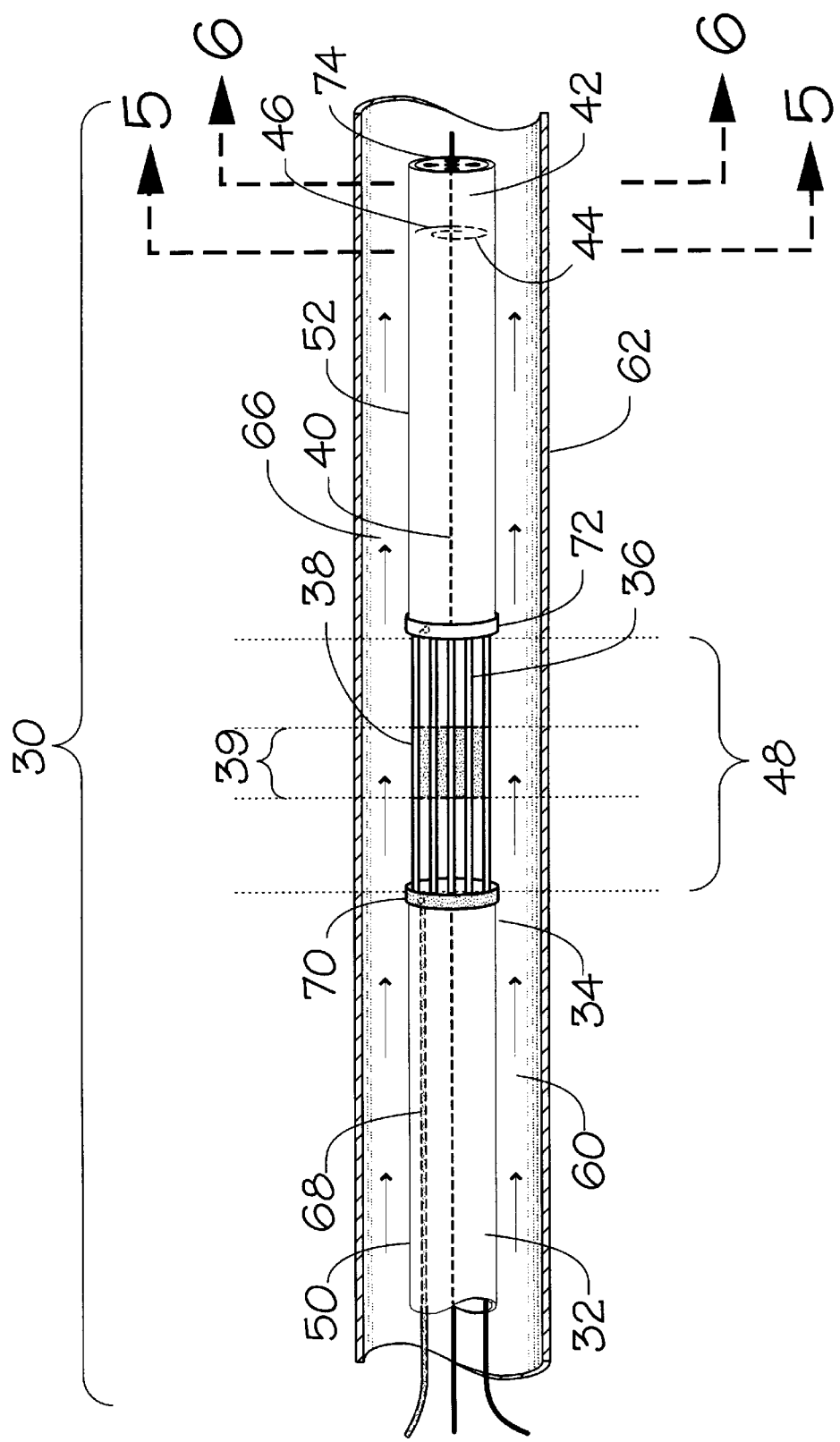
FIG. 4A is a side elevational view of an embodiment of the invention prior to deployment.

The embodiments of FIGS. 1–3C show the device in a bipolar configuration in which the flow of current through heating coil 36 is completed through the catheter. In the embodiment of FIG. 4A, catheter 30 is provided with a single current carrying wire 68 coupled to a terminal band 70 to which prebiased wire cage 38 is connected at one end and to a conductive ring 72 at its opposing end. Once again portions of 50 and 52 of catheter 30 can be pushed apart or drawn together by means of a guidewire 40 fitting into a screw or helical wire retainer 46 which is shown in plan view in FIG. 5. Distal end 74 of catheter 30 is illustrated in plan view as shown in FIG. 6 includes an end cap with a central bore 76 defined through end cap 78 to allow guidewire 40 to extend therethrough when it is screwed into retainer 46 as depicted in FIG. 4B. Also a plurality of peripheral holes 80 may also be defined through plate 78 to provide for blood flow through portion 52 of catheter 30 if desired. Although it is not anticipated that the interior of catheter 52 provide a path of substantial flow, some flow may nevertheless be desirable in order to minimize any tendency for clotting.

FIG. 4B illustrates the embodiment of FIG. 4A when portions 52 and 50 are drawn together thereby expanding cage 38 in the same manner as described in connection with FIGS. 2A and 2B. However, in the case of FIG. 4B wire 68 and ring 70 are insulated as are possibly the central portions 39 of the wires of cage 38 which wires serve as a means of holding the surrounding vessel walls and other tissue away from guidewire 40. Current is then supplied from external circuits 16 to uninsulated guidewire 40 whose exposed portion 48 coaxial inside of cage 38 acts as a electrode. Current flows from the exposed portion 48 of guidewire 40 through the surrounding blood 60 to grounded cage 38. Cage 38 is grounded by means of wire 68 leading back to circuits 16. The blood is therefore directly ohmically heated in the neighborhood of exposed portion 48 of guidewire 40, typically in a cylindrical volume within 1–2 mm of exposed portion 48 of guidewire 40. The blood flow in vessel 66 in turn is heated by conduction and convection processes from the heated neighborhood. In order the better localize and control the blood heating, only central portion 39 of guidewire 40 may be uninsulated which portion 48 lies within cage 38 or at least overlapping with it. The embodiment of FIGS. 4A and 4B represent a means by which a much more localized heating of the blood tissue occurs.

Figure 7:
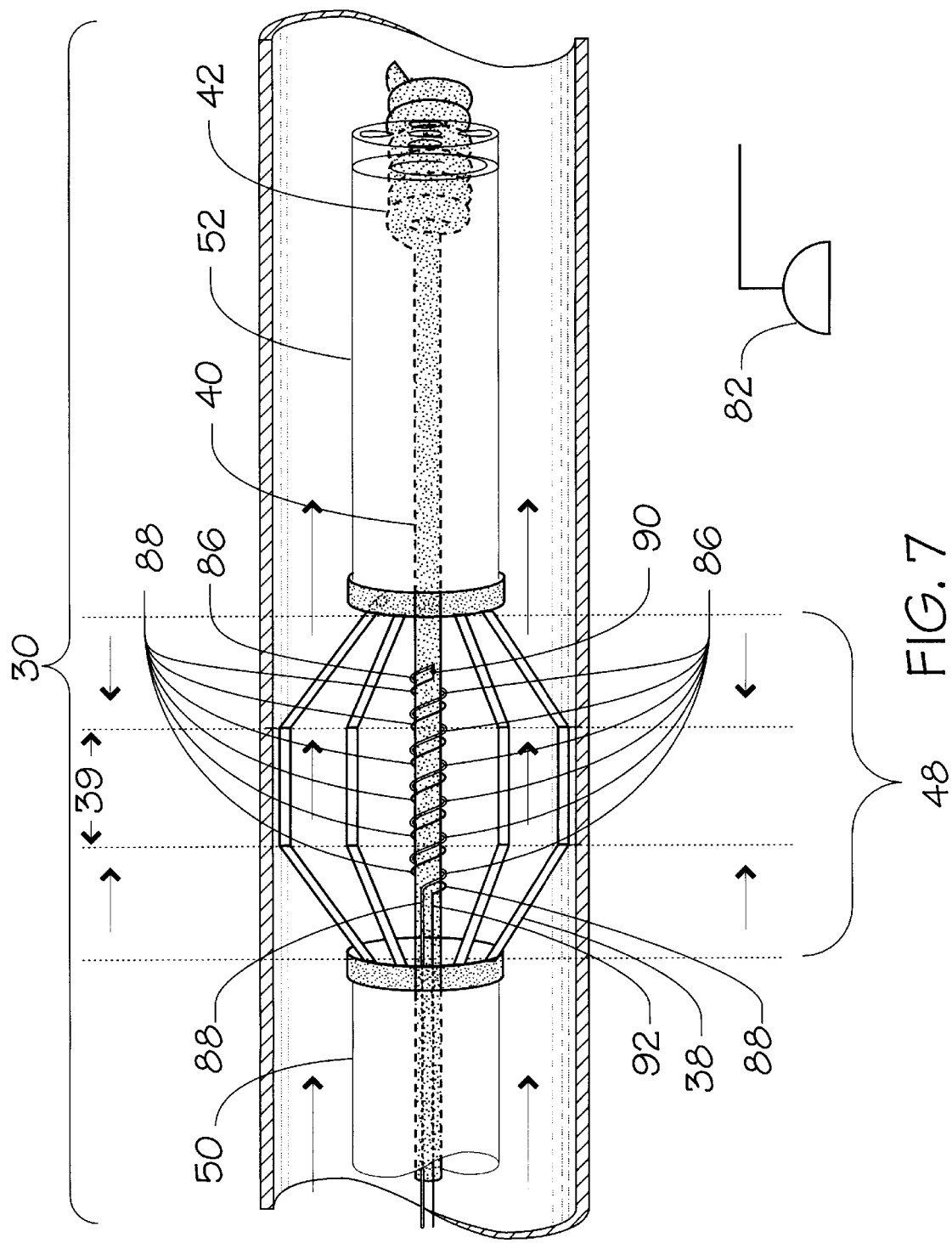
FIG. 7 is a side elevational view of a bipolar embodiment of the invention using the cage of FIGS. 4A and B.

FIG. 7 is a side elevational view in diagrammatic form of another embodiment of an invention in which guidewire 40 is provided with helical wrappings used in both a bipolar and unipolar mode. There are three forms of the heating coil arrangement on guidewire 40 and three forms of the cage extending radially outside of the coil. The heating coil may be a free, self-supporting coil itself or may be a winding on the guidewire. Where provided as a winding on the guidewire the heating coil may be: (1) a single uninsulated helix electrically coupled to the blood and completing the electrical circuit through a body electrode or ground pad 82 or a nearby catheter electrode (not shown); (2) a double insulated helix not electrically coupled to the blood and completing the electrical circuit only through the helix itself which forms a closed loop; or (3) a double uninsulated helix of two unconnected wires electrically coupled to the blood and completing the electrical circuit only through the blood lying in the gaps between the separate helical wraps. The three forms of the cage are: (1) the cylindrical barrel cage; (2) the biconical helical cage; and (3) a cylindrical helical cage. Any one or more of the three types of heating coils can be combined with any one or more of the three cages to yield at least nine distinguishable combinations, all of which are expressly included within the scope of the invention. Including self-supporting heating coils brings the number of expressly contemplated embodiments to 12. The provision of additional forms of the heating coil and cages according to the teachings of the invention may further multiply the embodiments which are possible.

It is to be understood that the guidewire design of FIG. 7 may be used in combination with the protective cage 38 or 64 as shown and described in FIGS. 1A–4B. For example, as shown in FIG. 7 in the bipolar mode, guidewire 40 may have an insulating film disposed upon it and a first uninsulated coil 86 connected at its proximate end to an insulated supply wire 89. Spirally wrapped on guidewire 40 and spaced from coil 86 is a second uninsulated coil 88. In this embodiment coils 86 and 88 are not connected to at point 90. The pitch of the wraps of coils 86 and 88 may be approximately one millimeter. The proximal end of coil 88 is then connected to its supply wire 92 which is also shown as insulated. Both coils 86 and 88 may be uninsulated from each other but spaced apart on an insulated portion of guidewire 40. Therefore, while current flows through coils 86 and 88 it is also provided and flows through the intervening blood tissues between adjacent wraps of coils 86 and 88 to not only ohmically heat coils 86 and 88, but also the immediately adjacent blood tissue. Alternatively, the resistance of coils 86 and 88 may be sufficiently low such that all the ohmic heating occurs only in the blood or fluid between the wire wraps.

It is also within the scope of the invention that both coils 86 and 88 may be both insulated electrically, but have a thin film insulation which does not impede thermal conduction to any significant extent or has an insulation which is thermally conductive. In this embodiment, coils 86 and 88 are electrical coupled together at point 90. As before coils 86 and 88 have a composition so they are highly resistive so that ohmic heating which occurs in coils 86 and 88 is conducted to the surrounding blood flow.

Still further, if desired in an alternative embodiment, one of the coils 86 and 88 may be insulated and the other uninsulated to have a return current path made through the body tissue to a body surface electrode or ground pad 82 or through cage 38 or 64 as described above as well as in the closed loop of coils 86 and 88. Thus different forms of the heating coil and the cages may be combined if desired.

Figure 8A:
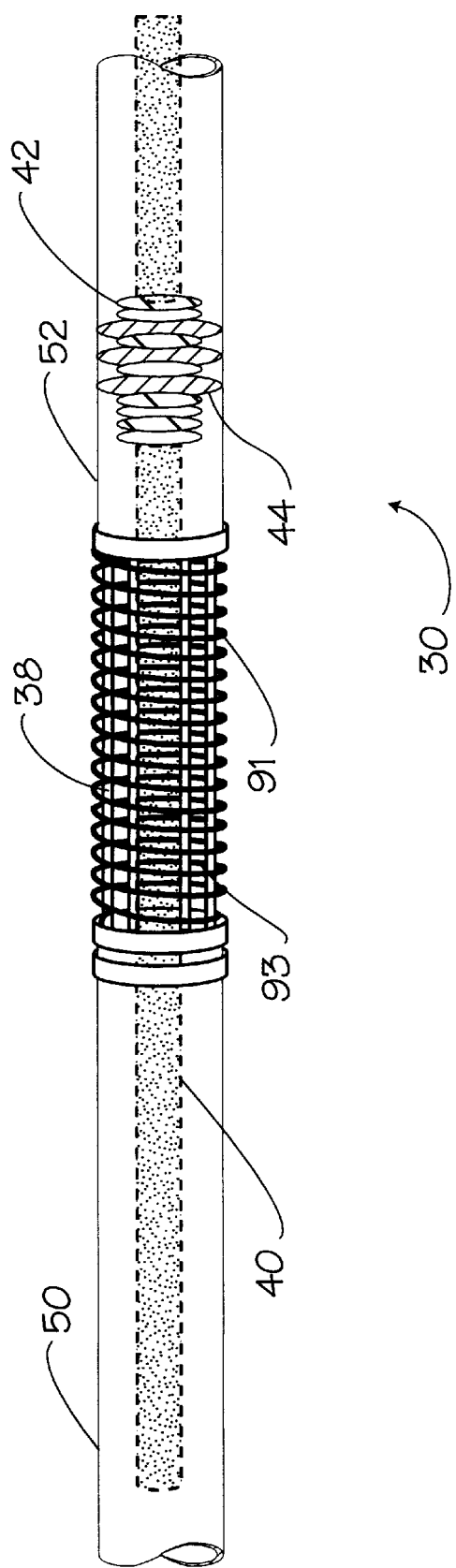
FIG. 8A is a side elevational view of an embodiment used in angioplasty prior to deployment.
Figure 8B:
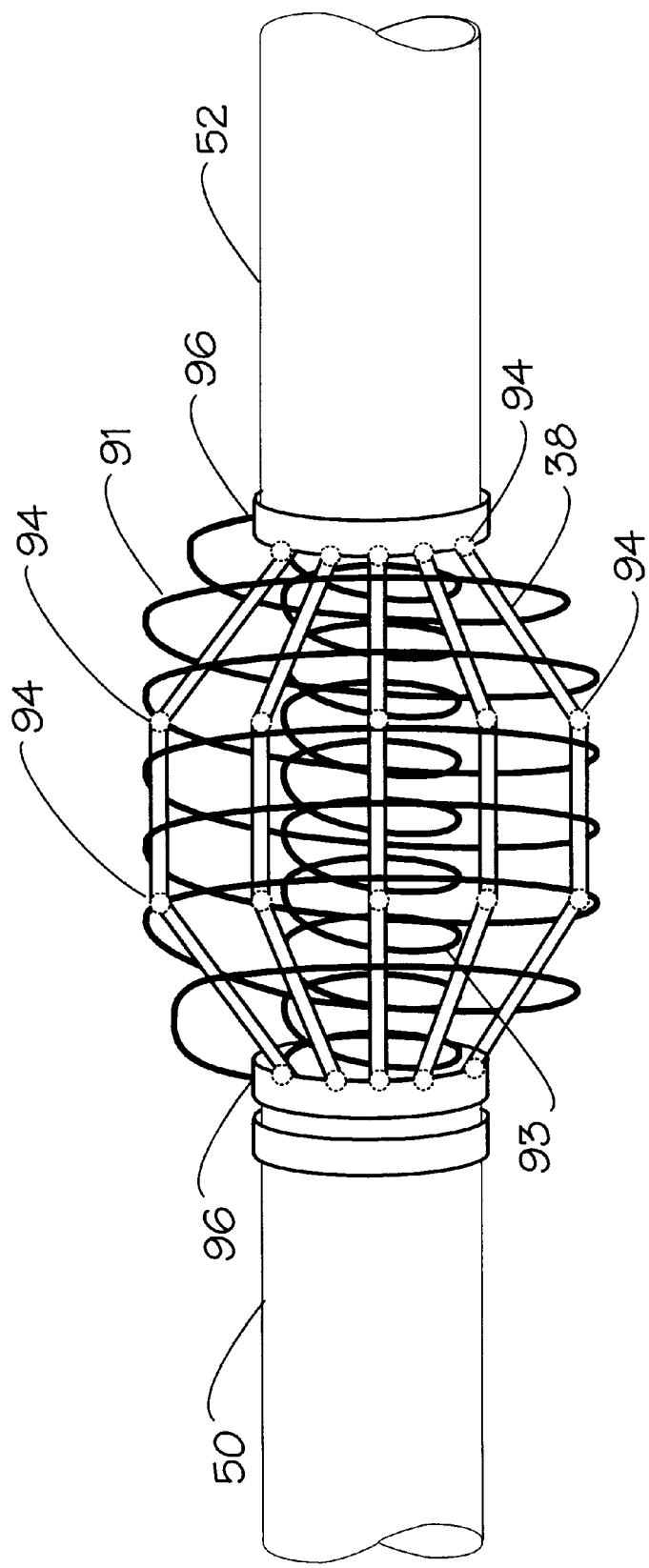
FIG. 8B is a side elevational view of the embodiment of FIG. 8A after deployment.

FIGS. 8A and B are side perspective views of an embodiment of the invention used in angioplasty. FIG. 8A shows catheter 30 in which an expandable cage 38 is coupled between portions 50 and 52 of catheter 30, which portions 50 and 52 are held apart by guidewire 40 which is threaded into threaded device 44. In FIG. 8A cage 38 is not deployed and thus is maintained in a shape and size similar to the outside envelope of catheter 30. An expandable helical cage or detachable stent 91 is deployed outside of cage 38 and connected at its ends to portions 50 and 52 of catheter 30. Helical cage 91 is also maintained in a shape and size similar to the outside envelope of catheter 30 by virtue of the engagement of guide wire 40 with device 44. Thus the cage assembly can be thought of as being made of two layers, an inner layer comprising cylindrical barrel cage 38 and an outer layer comprising helical cage 91. Also inside of cage 38 is a tension spring 93 which is better shown in FIG. 8B and which tends to push portions 50 and 52 of catheter 30 apart. Guidewire 40 when extended to its distal position as shown in FIG. 8A helps spring 93 to maintain portions 50 and 52 apart and cages 38 and 91 collapsed or nondeployed.

When guidewire 40 is withdrawn or pulled toward the proximal end of catheter 30, then cage 38 expands to assume a cylindrical barrel shape because of its memory of the prebiased shape formed into it. Points 94 are diagrammatically illustrated as the points where bends are prebiased in the wire forming cage 38 causing it to assume the expanded barrel configuration. At the same time, helical cage 91 outside of cage 38 also expands to a helical cylindrical shape because of its memory of the prebiased shape formed into it. The radially expanding shape of both cages 38 and 91 create a combined increased radial force for use in angioplasty applications. It is contemplated in the invention that the additional expansive force of spring 93 may not be needed in many applications and hence spring 93 may be omitted. In the preferred embodiment spring 93 is cylindrical and does not substantially change in radial size as it contracts or expands.

It is also contemplated that attachment points 96 of cage 91 to portions 50 and 52 may be selectively detachable by any means now known or later devised to allow cage 91 to be detached from catheter 30. In this case catheter 30 may then be removed leaving cage 91 in place as a stent. Detachment is accomplished in the illustrated embodiment by means of electrolytic detachment at points 96 by conventional means. In other words, attachment points 96 are comprised of a readily electrolyzable material and current is selectively supplied by a wire or wires (not shown) to points 96 resulting in their electrolytic disintegration and detachment of cage 91.

The advantage of an angioplasty device as shown in FIGS. 8A and B are twofold. First, the vascular expansion is accomplished by means of an open structure which has a minimal or at least tolerable interference on the vascular blood flow. In the case of balloon angioplasty the balloon entirely occludes the vessel when expanded, cutting off blood flow to all downstream tissues and organs, and thereby limiting the time during which the balloon may be expanded. If the balloon cannot be deflated when desired, then serious injury may result. In the case of cardiac or neural angioplasty the use of a balloon is fatally dangerous because of the possible deflation failure.

Second, some evidence tends to show that the ability of a vessel to expand without tearing or other damage and the tendency of the vessel to retain its expanded configuration, which is the end goal of angioplasty, is increased if the rate of expansion is slow and the time during which the expansion is artificially induced is long. The withdrawal of guidewire 40 may thus be mechanized by conventional means to occur gradually over a period of 30 minutes or more and then to be held in place with the cages in an expanded configuration for a similar length of time. Also during its slow expansion period the degree of the expansion, and the behavior of the vessel wall being treated can easily be monitored by simply injecting contrast agent through the catheter. Such protocols would be out of the question for any application of balloon angioplasty. Even if the vessel has a tendency to recollapse, the detachment of angioplasty cage 91 to act as a stent will provide the structural support to retain the vessel in an opened configuration. The ability to use the very device which caused the angioplastic expansion as the stent without withdrawal of the angioplasty catheter and insertion of a second catheter to place the stent not only reduces the amount of vascular trauma and damage, but insures that the stent placement always occurs at exactly the point of angioplastic expansion. The expandable cage 38 may have different configurations to ensure its expansive force. For example, instead of configuring the wires of the cage in parallel, the wires of cage 38 can be woven or braided.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for hyperthermic treatment of tissue comprising:

a catheter having a longitudinal lumen;

an elongated member having a distal and proximal end, said distal end adapted to be positioned proximate to said tissue and thermally coupled thereto, said elongated member telescopically disposed in said lumen of said catheter; and a ohmic heating element disposed on said elongated member at or proximate to said distal end, said ohmic heating element adapted to be in direct contact with fluid normally flowing to said tissue so that said tissue is subjected to a controlled amount of heat at a selected temperature for a selected amount of time, wherein said tissue is supplied with fluid by a vessel having a vascular wall; and a radially extensible cage structure for selectively maintaining said ohmic heating element in a spaced apart relationship from said vascular wall, and wherein said elongated member is variably coupled to said catheter so that an action applied to said elongated member is adapted to reversibly longitudinally elongate or contract at least a distal portion of said catheter and thereby to reversibly and radially extend or contract said cage structure.

2. The apparatus of claim 1 further comprising a temperature sensor to detect temperature of said fluid downstream from said ohmic heating element to provide a feedback control signal to control power provided to said coil heating element.

3. The apparatus of claim 2 further comprising a power source coupled to said ohmic heating element and provided with said feedback control signal to control said power provided by said power source to said ohmic heating element according to temperature of said fluid downstream from said ohmic heating element.

4. A method for hyperthermically treating tissue comprising:

providing a catheter having a longitudinal lumen;

providing an elongated member with a ohmic heating element included within a distal portion of said elongated member, said elongated member telescopically disposed in said lumen of said catheter;

disposing said distal portion of said elongated member proximate to tissue to be treated at a position thermally coupled to said tissue through fluid flow thereto;

maintaining said distal portion of said elongated member out of contact with surrounding tissue except for said fluid flowing by said distal portion of said elongated member; and selectively providing power to said ohmic heating element to heat fluid flowing by said ohmic heating element to said tissue to be treated, wherein said tissue is supplied with fluid by a vessel having a vascular wall; and a radially extensible cage structure for selectively maintaining said ohmic heating element in a spaced apart relationship from said vascular wall when said power is provided to said ohmic heating element, and wherein said elongated member is variably coupled to said catheter and further comprising applying an action to said elongated member to reversibly longitudinally elongate or contract at least a distal portion of said catheter and thereby to reversibly and radially extend or contract said cage structure.

5. A method for hyperthermically treating tissue comprising:

providing a elongated member having a proximal end with a ohmic heating element included within a distal portion of said elongated member;

disposing said distal portion of said elongated member proximate to tissue to be treated at a position thermally coupled to said tissue through fluid flow thereto;

maintaining said distal portion of said elongated member out of contact with surrounding tissue except for said fluid flowing by said distal portion of said elongated member; and selectively providing power to said ohmic heating element to heat fluid flowing by said ohmic heating element to said tissue to be treated, where maintaining said distal portion of said elongated member out of contact with surrounding tissue except for said fluid flowing by said distal portion of said elongated member comprises deploying an expandable cage around said ohmic heating element, where deploying an expandable cage around said ohmic heating element comprises longitudinally drawing a distal portion of said elongated member toward said proximal end of said elongated member to shorten said expandable cage thereby radially extending said expandable cage deployed about said ohmic heating element without substantially radially extending said ohmic heating element.

* * * * *